US00PP18900P2

(12) United States Plant Patent
Bessho et al.

(10) Patent No.: US PP18,900 P2
(45) Date of Patent: Jun. 10, 2008

(54) ***CALIBRACHOA* PLANT NAMED 'KAKEGAWA S86'**

(50) Latin Name: ***Calibrachoa* sp.**
Varietal Denomination: Kakegawa S86

(75) Inventors: Masao Bessho, Kakegawa (JP); Akinobu Ui, Iwata (JP)

(73) Assignee: Sakata Seed Corporation, Yokohama (JP)

( * ) Notice: Subject to any disclaimer, the term of this patent is extended or adjusted under 35 U.S.C. 154(b) by 17 days.

(21) Appl. No.: 11/699,513

(22) Filed: Jan. 29, 2007

(51) Int. Cl.
*A01H 5/00* (2006.01)

(52) U.S. Cl. ..... Plt./263
(58) Field of Classification Search ..... Plt./263
See application file for complete search history.

*Primary Examiner*—Annette H Para
(74) *Attorney, Agent, or Firm*—Jondle & Associates, P.C.

(57) ABSTRACT

'Kakegawa S86' is a new *Calibrachoa* cultivar particularly distinguished by having a yellow flower color and a compact growth habit.

1 Drawing Sheet

Genus and species: *Calibrachoa* sp.
Variety denomination: 'Kakegawa S86'.

BACKGROUND OF THE INVENTION

The present invention comprises a new and distinct cultivar of *Calibrachoa,* botanically known as *Calibrachoa* sp., and hereinafter referred to by the cultivar name 'Kakegawa S86.' It is characterized by having yellow flower color and compact plant growth habit. The new cultivar originated from a hybridization made in 2002 in Kakegawa, Japan. The female parent was a proprietary hybrid *Calibrachoa* breeding line named 'S-24A-23' having a scarlet flower color and a semi-upright plant growth habit. The male parent was a proprietary hybrid *Calibrachoa* breeding line named '1B-69B' characterized by its yellow flower color and compact plant growth habit.

In 2002, 'S-24A-23' and '1B-69B' were crossed and 32 seeds were obtained in 2003, $F_2$ seed was sown in the greenhouse and 78 plants were evaluated. $F_2$ plants were segregated into scarlet and yellow flower color and all plants had a compact plant growth habit. Two single-plant selections were made based to their yellow flower color and compact plant growth habit and vegetatively propagated.

In 2004, plantlets of the two lines were transplanted to soilless media for greenhouse culture, vegetatively propagated with cuttings in Kakegawa and then re-evaluated. The line 'K4-162' was selected and grown in an open field trial to confirm the stability of the distinct characteristics of this line. The line was subsequently named 'Kakegawa S86' and its unique characteristics were found to reproduce true to type in successive generations of asexual propagation.

Plant Breeder's Rights for this cultivar were applied for in Canada in Mar. 31, 2006.

DESCRIPTION OF THE GENUS CALIBRACHOA LLAVE & LEX.

The genus *Petunia* was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida,* the Garden *Petunia,* and the inter-relationship of several species classified as *Petunia*. These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the *Petunia* genus, Wijsman and J. H. de Jong proposed transferring the 14 chromosome species to the genus *Stimoryne.* Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, and a single outermost petal covers the other four, radially folded and terminally contorted petals. *Calibrachoa* flower buds are flat with all five petals linearly folded and the two lower petals forming a cover around the three other petals and fused together.

SUMMARY OF THE INVENTION

The following are the most outstanding and distinguishing characteristics of this new cultivar when grown under normal horticultural practices in Kakegawa, Japan.

1. Yellow flower color; and
2. Compact plant growth habit.

DESCRIPTION OF PHOTOGRAPHS

This new *Calibrachoa* plant is illustrated by the accompanying photographs which show the plant's form, foliage and flowers. The colors shown are as true as can be reasonably obtained by conventional photographic procedures.

DESCRIPTION OF THE NEW CULTIVAR

Figure 1:
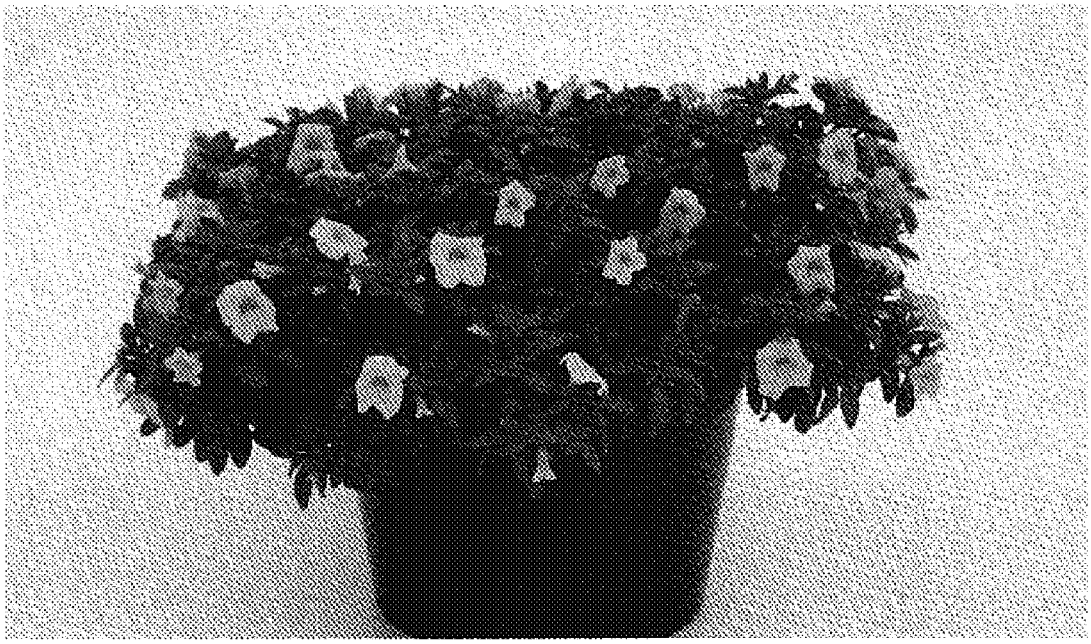
FIG. 1 shows overall plant habit.
Figure 2:
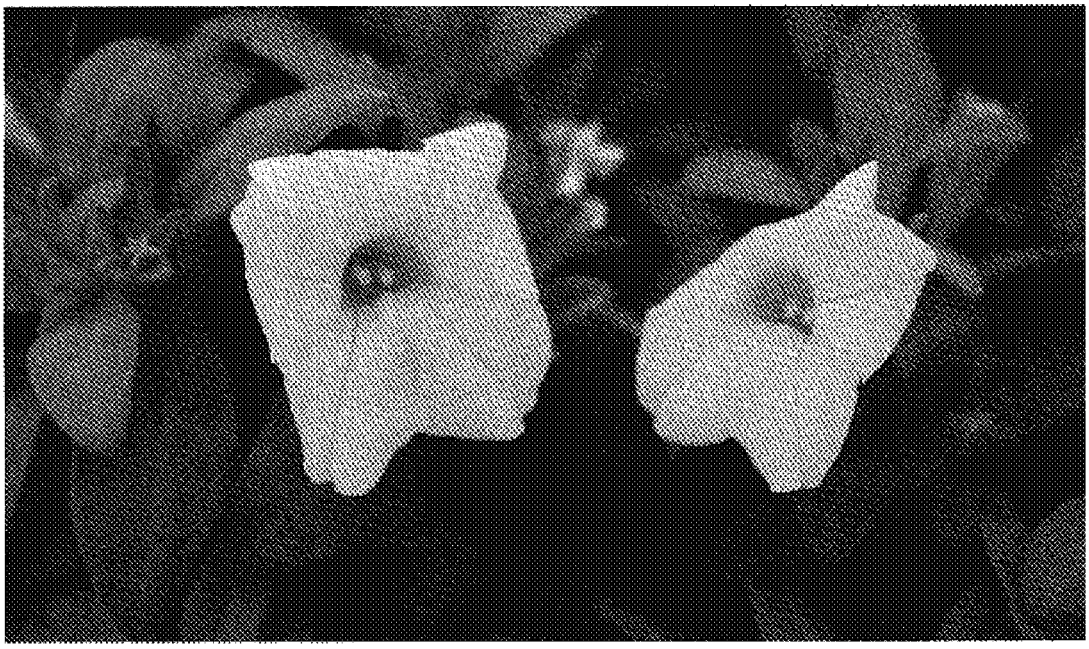
FIG. 2 shows the mature flowers.

The following detailed description sets forth the distinctive characteristics of 'Kakegawa S86'. The data which define these characteristics were collected from asexual reproductions carried out in Salinas, Calif. The detailed description was taken from plants grown under greenhouse conditions for approximately 6 months from transplanting of rooted cuttings. Color references are to the R.H.S. Colour Chart at The Royal Horticultural Society of London (RHS), $4^{th}$ Edition.

DETAILED BOTANICAL DESCRIPTION

Classification:
- *Family.*—Solanaceae.
- *Species.*—*Calibrachoa* sp. Cultivar 'Kakegawa S86'.
- *Common name.*—*Calibrachoa.*

Parentage:
- *Male.*—Hybrid proprietary *Calibrachoa* breeding line '1B-69B'.
- *Female.*—Hybrid proprietary *Calibrachoa* breeding line 'S-24A-2'.

Plant description:
- *Life cycle.*—Tender perennial.
- *Form.*—Branching.
- *Habit.*—Mounding.
- *Height.*—9.0 cm to 11.0 cm.
- *Spread.*—25 cm to 35 cm.

Propagation:
- *Type cuttings.*—Vegetative cuttings.
- *Time to produce a rooted cutting.*—6 weeks.
- *Time to bloom from propagation.*—10 weeks.

Environmental conditions for plant growth: The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Stems:
- *Stem color.*—RHS 144C (Green).
- *Anthocyanin color.*—Absent.
- *Pubescence.*—Slight.
- *Pubescence color.*—RHS 155A (White).
- *Stem description.*—Round.
- *Stem diameter.*—0.1 cm to 0.2 cm.
- *Stem length.*—2.0 cm to 2.5 cm.
- *Internode length.*—0.3 cm to 0.4 cm.

Leaves:
- *Arrangement.*—Alternate.
- *Shape.*—Elliptical.
- *Apex.*—Obtuse.
- *Base.*—Attenuate.
- *Attachment.*—Sessile.
- *Margin.*—Entire.
- *Surface.*—Dull.
- *Surface pubescence.*—Slight.
- *Pubescence color.*—RHS N155A (white).
- *Venation.*—Pinnate.
- *Length.*—3.0 cm to 3.5 cm.
- *Width.*—0.8 cm to 1.2 cm.
- *Color.*—Upper surface: RHS 137B (Green). Lower surface: RHS 138B (Green).
- *Fragrance.*—Absent.

Flowers:
- *Flowering habit.*—Indeterminate.
- *Flower type.*—Solitary.
- *Flowering requirements.*—Will flower so long as day length is greater than 12 hours and temperature exceeds 13° C.
- *Duration of flowers.*—About 5 days.
- *Corolla.*—5 petals, fused.
- *Corolla shape.*—The flowers are funnel shaped with five fissures and a shallow, yet slight, indentation of the petal tip at the midvein.
- *Fragrance.*—Absent.

Flower buds:
- *Surface.*—Pubescent.
- *Length.*—1.0 cm.
- *Diameter.*—0.2 cm to 0.3 cm.
- *Shape.*—Ovate.
- *Color.*—RHS 150C (Yellow-green).
- *Peduncle.*—Length: 1.0 cm. Color: RHS 144C (Green).

Flower description:
- *Flower depth.*—2.0 cm to 2.5 cm.
- *Flower tube length.*—1.0 cm.
- *Flower tube diameter.*—0.2 cm to 0.3 cm.
- *Flower diameter.*—2.5 cm to 3.0 cm.
- *Calyx.*—5 sepals fused at the middle.
- *Sepals.*—Shape: Elliptical. Apex: Obtuse. Margin: Entire. Sepal color: RHS 141B (Green).
- *Petals.*—Shape: Spatulate. Length: 1.0 cm. Width: 0.3 cm to 0.4 cm. Apex: Truncate. Margin: Entire. Texture: Glabrous. Color: Limb color: Upper surface: Closest to RHS 12B (Yellow). Lower surface: Closest to RHS 8B (Yellow). Corolla tube color: Inner: RHS 12B (Yellow-orange). Outer: RHS 8B (Yellow).
- *Fragrance.*—Absent.

Reproductive organs:

*Stamen number.*—5 free.

*Stamen color.*—Anther color is RHS 5B (Yellow). Filament color: RHS 150C (Yellow-green).

*Pollen color.*—RHS 5B (Yellow).

*Ovary.*—Superior.

*Placenta arrangement.*—Central.

*Pistil number.*—1.

*Pistil length.*—0.1 cm.

*Stigma color.*—RHS 141C (Green).

*Style length.*—0.1 cm.

*Style color.*—RHS 141C (Green).

Fruit/seed set: No fruit or seeds produced.

Disease and insect resistance: 'Kakegawa S86' has excellent resistance to rain, heat and drought. It will not tolerate temperatures below 10° C. Plants are susceptible to *Botrytis,* powdery mildew, various stem and root rots, and certain viruses, like Tobacco Mosaic Virus and Impatiens Necrotic Spotted Virus. Plants can be infested with aphids, leafminer, whitefly and various *Lepitopdera.*

COMPARISON WITH PARENTAL LINES AND KNOWN CULTIVARS

'Kakegawa S86' is distinguished from its parents mainly by flower color and plant growth habit as shown in Table 1 below.

TABLE 1

| Characteristic | 'Kakegawa S86' | Female Parent: 'S-24A-23' | Male Parent: '1B-69B' |
|---|---|---|---|
| Flower color | Yellow | Scarlet | Yellow |
| Plant growth habit | Creeping | Semi-upright | Compact |

*Calibrachoa* 'Kakegawa S86' is a distinct variety of *Calibrachoa* due to its yellow flower color and compact growth habit. 'Kakegawa S86' is most similar to the variety 'Kakegawa S46' (U.S. Plant Pat. No. 14,779) however, there are differences in the flower color and plant growth habit as described in the table below (color references are to The Royal Horticultural Society Colour Chart, $4^{th}$ edition):

TABLE 2

| Characteristic | 'Kakegawa S86' | 'Kakegawa S46' |
|---|---|---|
| Petal color, upper surface | RHS 12B (Yellow) | RHS 4D (Yellow) |
| Plant growth habit | Very compact | Compact |

We claim:

1. A new and distinct cultivar of *Calibrachoa* plant as shown and described herein.

* * * * *